United States Patent [19]
Hsiue et al.

[11] Patent Number: 6,005,160
[45] Date of Patent: Dec. 21, 1999

[54] HETEROBIFUNCTIONAL MEMBRANE IN APPLICATION OF ARTIFICIAL CORNEA

[75] Inventors: Ging-Ho Hsiue, Hsinchu; Shyh-Dar Lee, Taipei; Patricia Chuen-Tsuei Chung, Taichung, all of Taiwan

[73] Assignee: National Science Council, Taipei, Taiwan

[21] Appl. No.: 08/604,903

[22] Filed: Feb. 22, 1996

[51] Int. Cl.$^6$ .................................. A61F 2/02; A61F 2/14
[52] U.S. Cl. ....................................... 623/11; 623/6
[58] Field of Search ..................... 623/4, 5, 7, 8, 623/11, 12, 13–16

[56] References Cited

U.S. PATENT DOCUMENTS 4,806,382  2/1989  Goldberg et al. .
5,376,400  12/1994  Goldberg et al. ................ 427/2.24

FOREIGN PATENT DOCUMENTS 333344  9/1989  European Pat. Off. .
342895  11/1989  European Pat. Off. .

OTHER PUBLICATIONS

Girard, et al., Keratoprosthesis: A 12–Year Follow–Up, Transactions–American Academy of Ophthalmology & Otolaryngology, 83(2), 252–267, 1977.
Cardona, Mushroom Transcorneal Keratoprosthesis, American J. Ophthal, 68, No. 4, 604–612, 1969.
Kirkham, et al., The Keratoprosthesis: Improved Biocompatability Through Design and Surface Modification, Ophthalmic Surgery, 22, No. 8, 455–461, 1991.
Kobayashi, et al., Collagen–Immobilized Hydrogel as a Material for Lamellar Keratoplasty, J. Applied Biomaterial, 2, 261–267, 1991.

Primary Examiner—David J. Isabella
Assistant Examiner—John M. Black
Attorney, Agent, or Firm—Beveridge, DeGrandi, Weilacher & Young, LLP

[57] ABSTRACT

This invention is a heterobifunctional artificial cornea or biomedical membrane and novel process for preparing the heterobifunctional artificial cornea. In this method, plasma induced graft polymerization is adopted to provide the surface property modification of polymer materials like silicone or polyurethane. At first, the frontal side of the material is grafted with polyacrylic acid or polymethacrylic acid and then bonded with collagen, or 2-hydroxyethylmethacrylate (HEMA) is grafted alone. A surface which increases the cell attachment and growth can be then developed. Another side of this membrane is grafted with acrylic acid or polymethacrylic acid and then different molecular weights of polyethylene oxide (PEO) is bonded thereto. 2-methacryloyl-oxyethyl phosphoryl chloride (2-MPC) is grafted to the membrane. The copolymer of the 2-methacryl-oyloxyethyl phosphoryl chloride and MPC-co-butyl methacrylate can be used in preparing a special surface which can inhibit the attachments of cells and protein molecules. Thus, a heterobi-functional biomedical membrane can be developed. In this work, the surface characterization of this membrane, in vitro study and animal in vivo study are also investigated. The obtained results exhibit a very good performance. Moreover, it demonstrates that the developed product has good transparency, hydrophilicity and high biocompatibility, thereby exhibiting the high potential in the application field of artificial cornea.

13 Claims, 26 Drawing Sheets

(21 of 26 Drawing Sheet(s) Filed in Color)

Enhanced layer

Suppressed layer

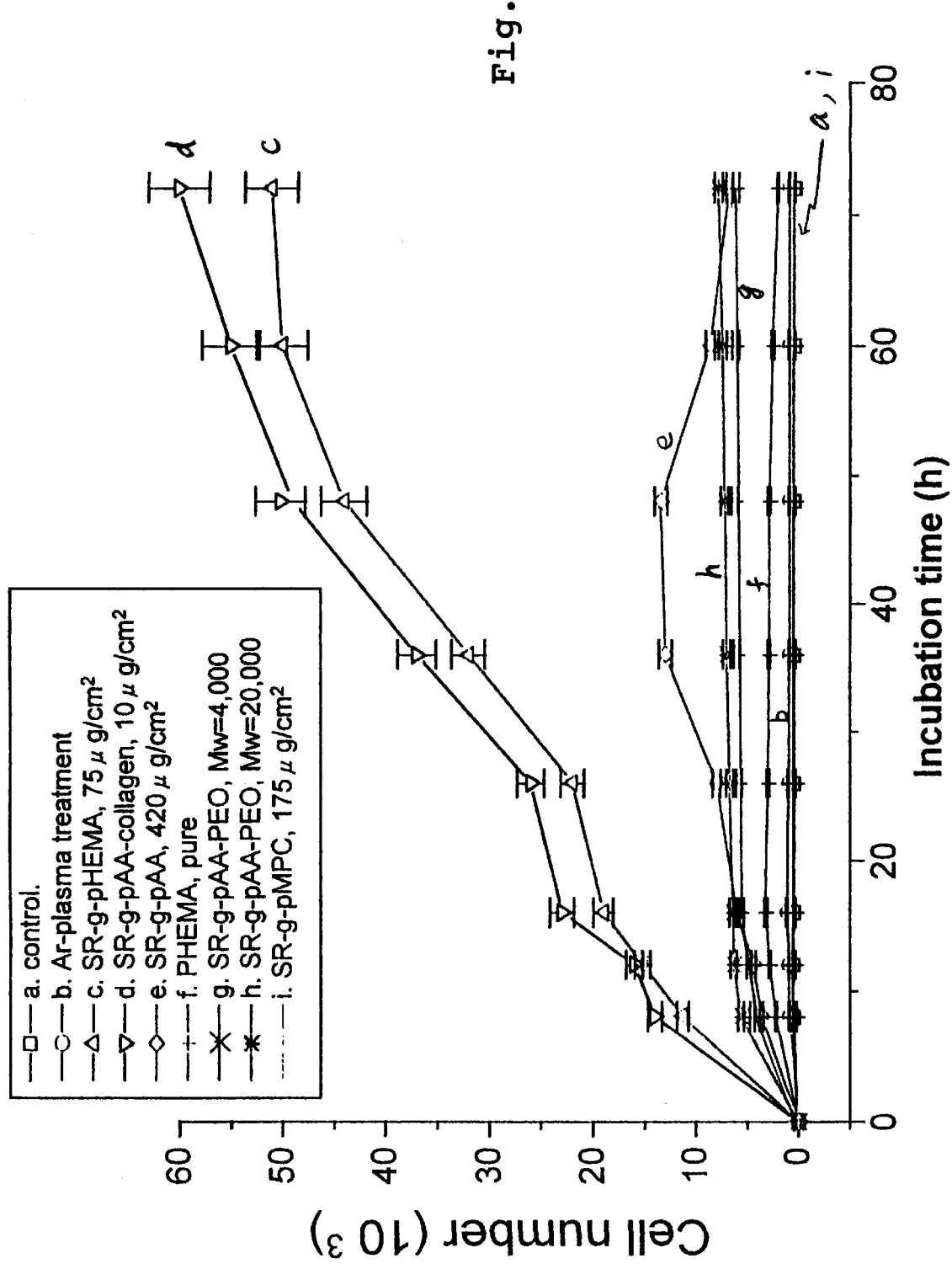

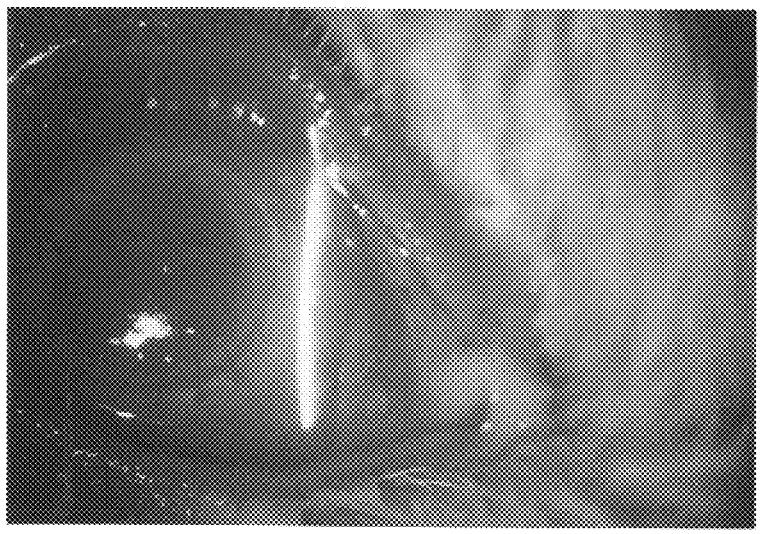
Fig. 11A

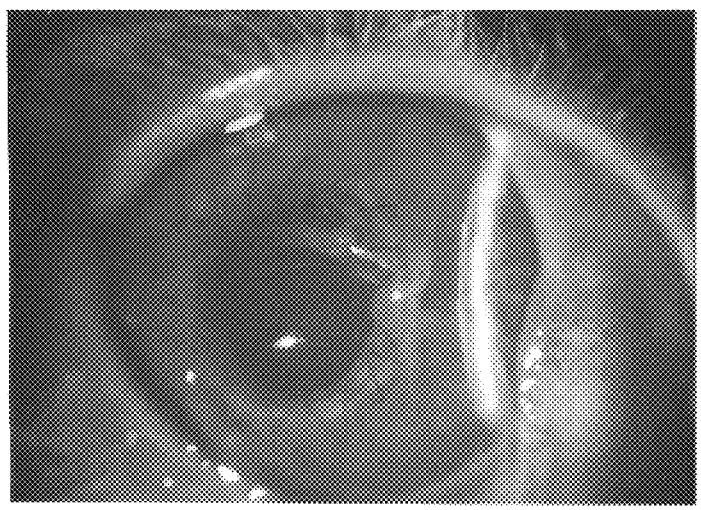 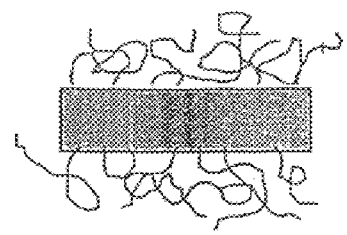
Fig. 11B

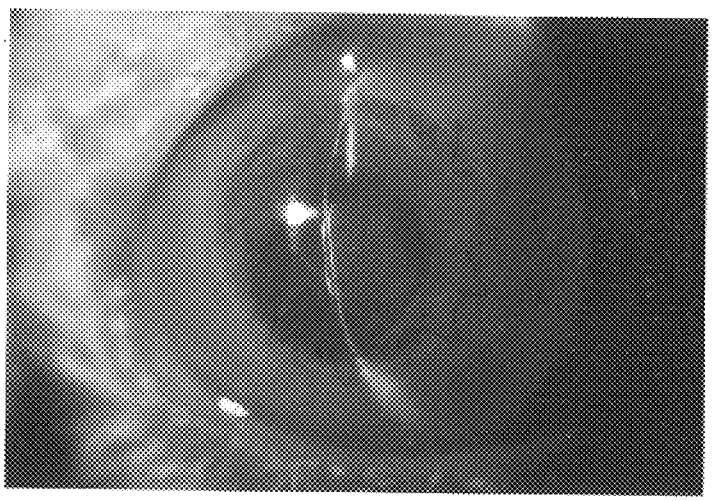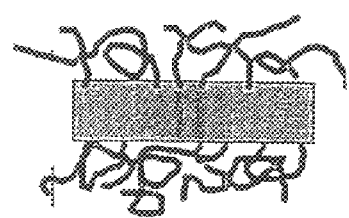
Fig. 11C

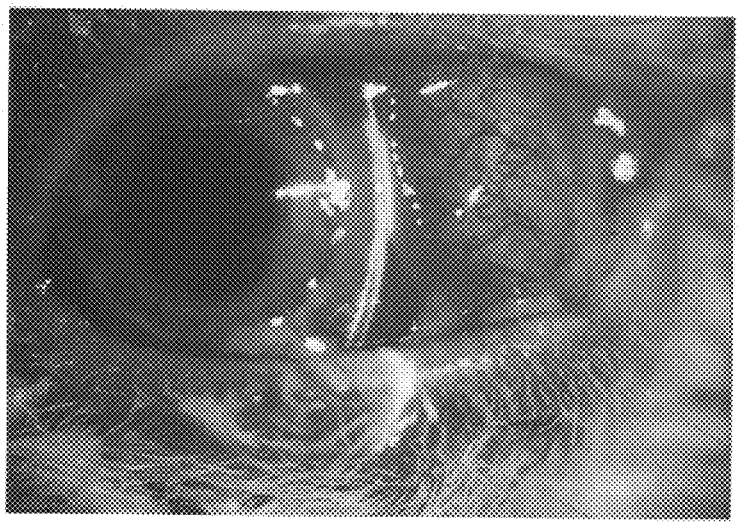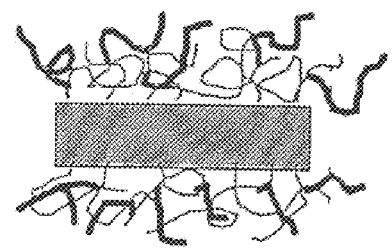
Fig. 11D

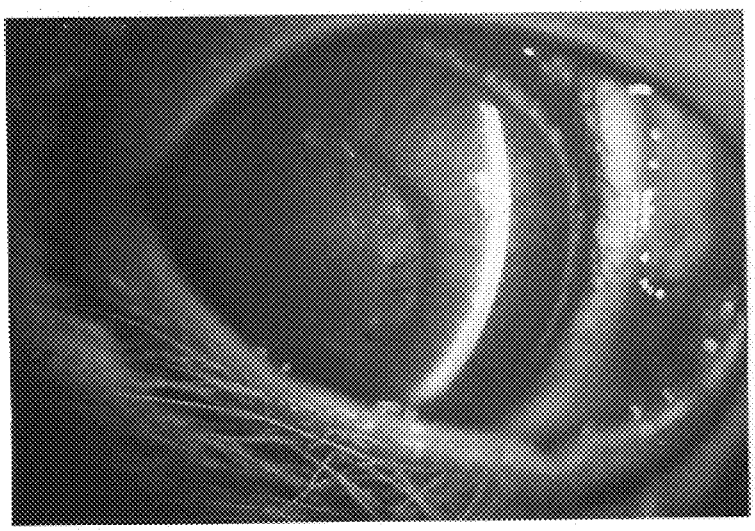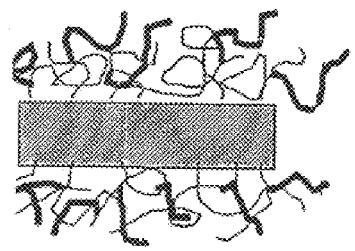
Fig. 11E

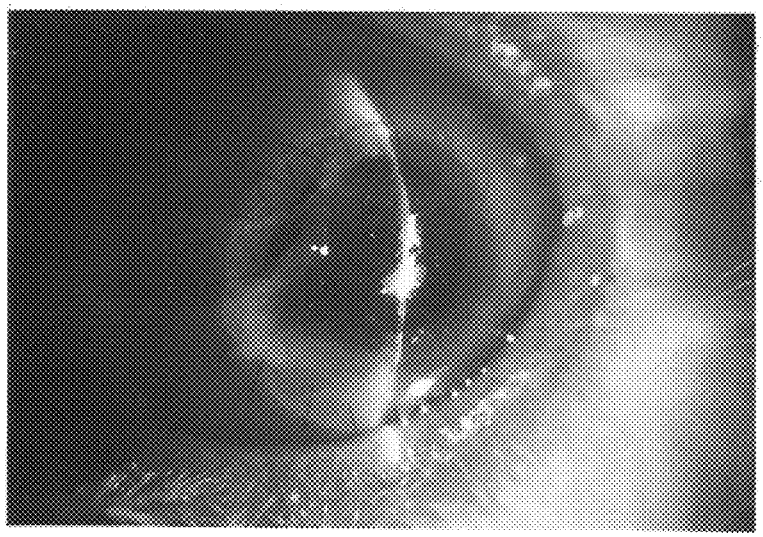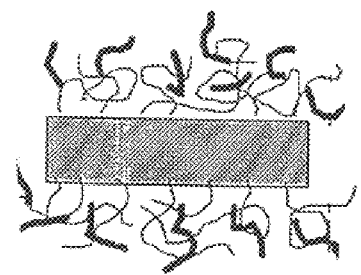
Fig. 11F

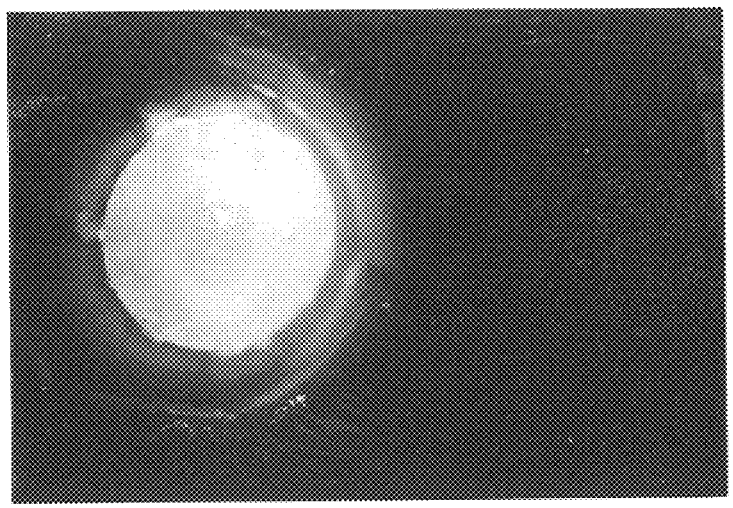
Fig. 12A

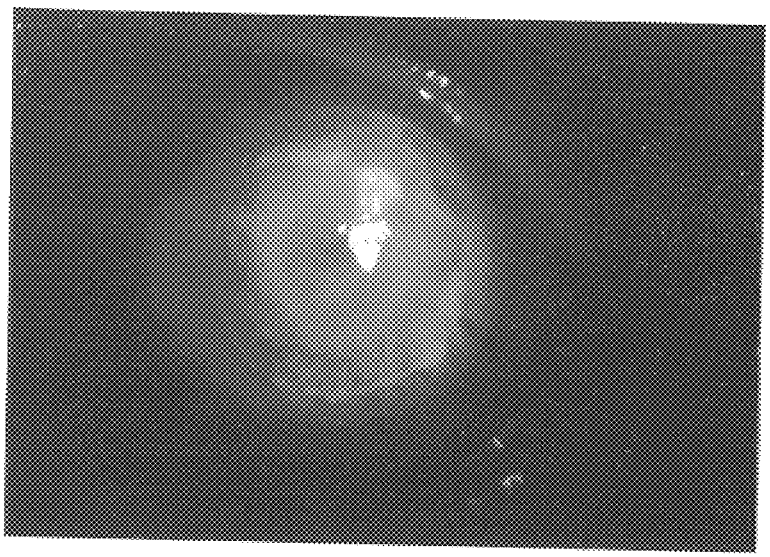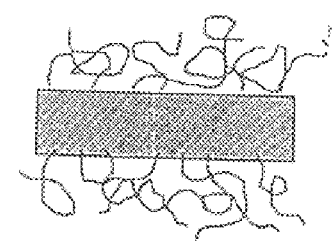
Fig. 12B

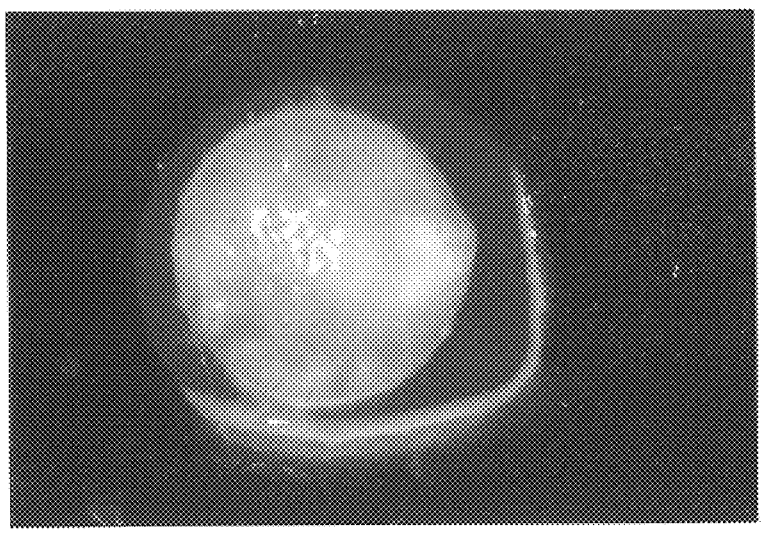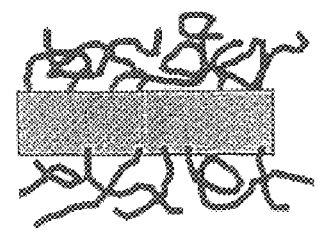
Fig. 12C

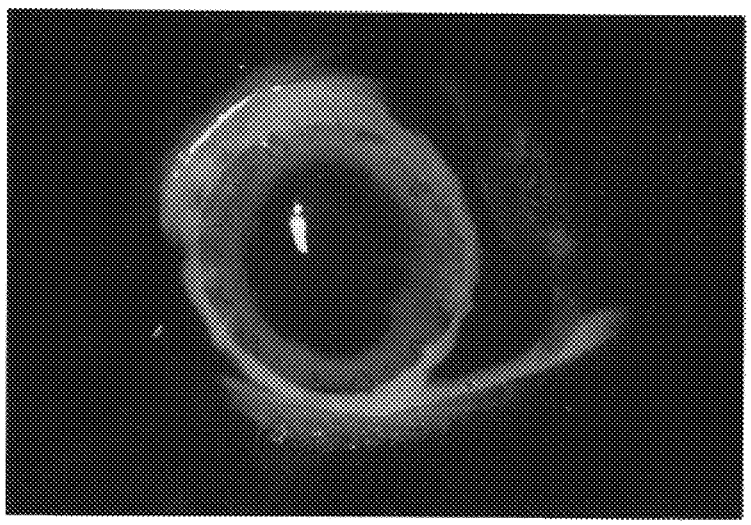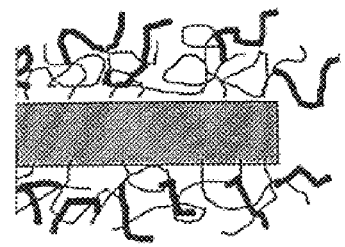
Fig. 12D

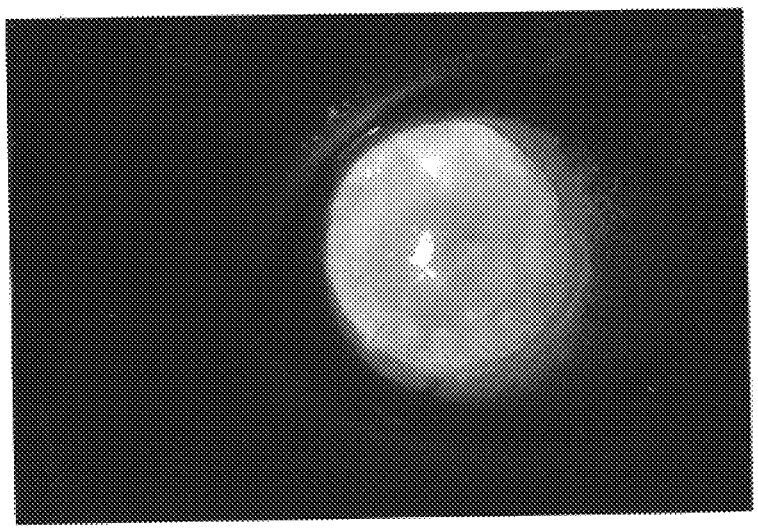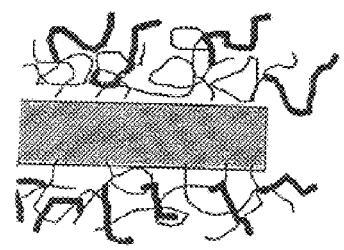
Fig. 12E

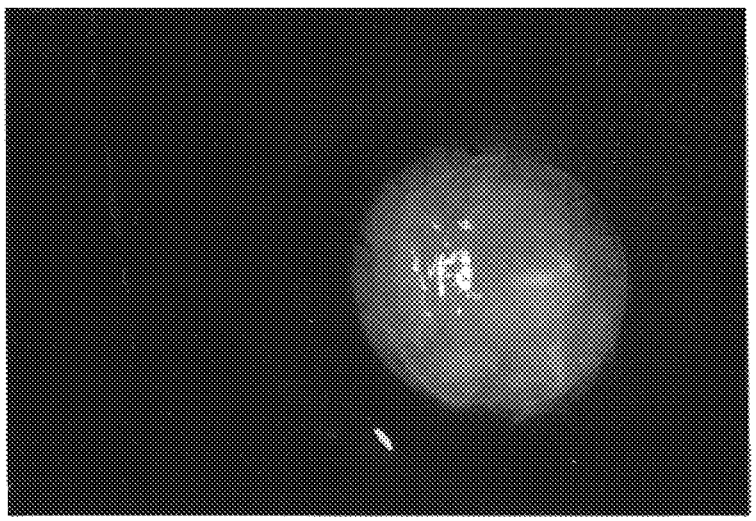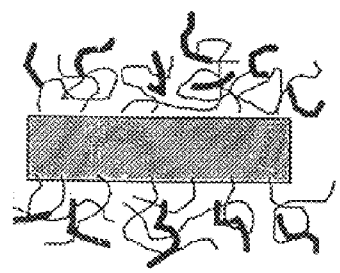
Fig. 12F

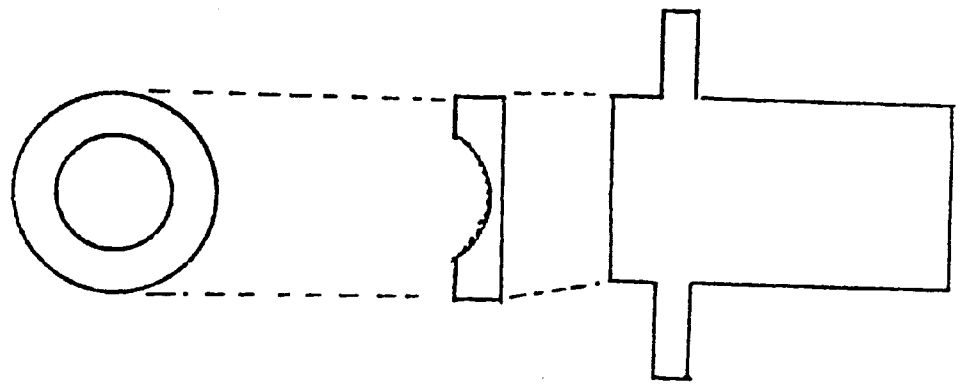
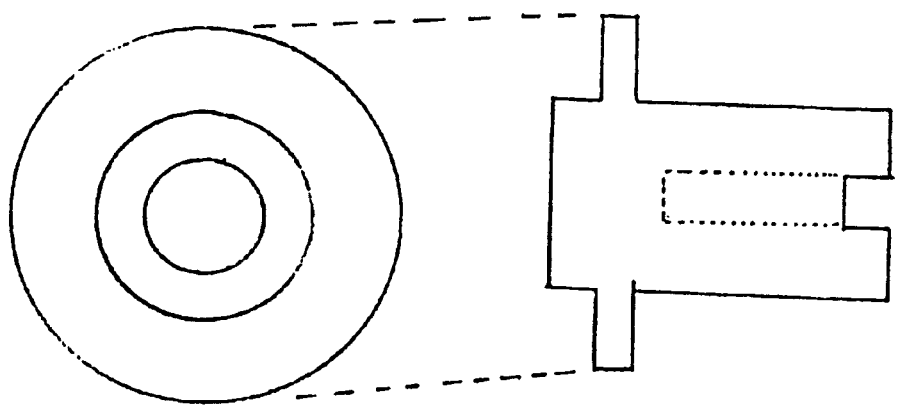
Fig. 14

HETEROBIFUNCTIONAL MEMBRANE IN APPLICATION OF ARTIFICIAL CORNEA

DESCRIPTION OF THE INVENTION

1. Background of the Invention

As well known, in the field of biomedical material of artificial corneas, commonly, it is may be necessary to implement a whole layer or divided layer complex cornea implant operation for maintaining the integrity of an eyeball and avoid further complications. A progressive cornea ulceration can lead to a penetrating cornea injury or whole layer cornea injury with tissue loss which occurs. For example, the extensive chamber angle synechia may lead to angle closure glaucoma or internal eye complications. The emergent operation can reduce the possible sight injury.

In Taiwan, due to the limitation of religion, the donation of organs is not very common, and a source of corneas is rare. Presently, the main sources of donated corneas which are used in cornea implants are Sri Lanka and U.S. These sources can not satisfy the demands for emergent cornea implant operations. Presently, the curing procedure for this kind of disease still uses the residue sclera tissue of donated cornea to mend onto a penetrating hole. This treating process can activate the epithelial cells of cornea to grow smoothly, but, it is inevitable that the internal cornea substrate incorporates the exotic vein tissue simultaneously, so, many annoyances will be created in proceeding with the cornea implant operation in the future.

The preparation method of an ideal and permanent artificial cornea that possesses biological compatibility is a landmark in ophthalmology. It is especially important to the cornea operation doctors in Taiwan. A temporary artificial cornea that has biological compatibility and keeps the cornea functional for three months, at least on the donated cornea, is attempted to be prepared before the permanent artificial cornea material is found. This temporary artificial cornea can be pushed by the cornea epithelial cells (CEC) with re-implant growth, and thus eye ball roundness can be kept temporarily. Under the inflame stable status, the eyeball surface can provide a better implant environment before the cornea is implanted.

In the past years, the relevant research in this field is the following: Cardona H. M. D. et al. (1969, American J. Ophthal, Vol. 68, No. 4, PP. 604–612) developed a plastic fiber meshwork supporting plate which is a cylinder shape, is migrated into the eye directly, and is named the Cardona implant. Giard L j, M.D. (1977) modified this implant mentioned above to be the secondary generation Giard Keratoprosthesis. Kirkham S M, M.D. et al. (1991, Ophthalmic Surgery, Vol. 22, No. 8, pp. 455–461) developed a method for preparing the artificial membrane using the surface coating collagen on the surface of polymethylmethacrylate (PMMA) to increase the biological compatibility of the implant. Kobayashi, H. et al. (1991, J. Applied Biomaterial, Vol. 2, pp. 261–267) introduced the preparation method of the artificial cornea. Collagen grafts on the surface of a PVC plate and this membrane are implanted into a rabbit cornea with a stratified implant operation.

However, in the patent application side, Eugene, P. G. et al. (1991, U.S. Pat. No. 806382) introduced an internal eye implant which is prepared with four materials, namely polypropylene (PP), polyvinyfloride (PVF), polymethylmethacrylate (PMMA), and PC. The product described above is irradiated by a Co 60 ray and then grafted with 2-hydroxyethyl methacrylate (HEMA) or N-vinylpyrrolidone (VP) for improving the product surface biological compatibility.

SUMMARY OF THE INVENTION

The main purpose of this invention is to provide an artificial cornea which has high biological compatibility, and which includes a surface multifunctional biomedical membrane that possesses good transparency and hydrophilicity. In particular, the invention relates to a heterobifunctional biomedical membrane which comprises a polymer substrate membrane, an enhanced layer, and a suppressed layer.

This invention also provides a preparation method of the heterobifunctional biomedical membrane. According to the plasma induced graft polymerization, a selected polymer material is prepared as the polymer substrate membrane. Then some perfected polymer materials, as an enhanced layer and a suppressed layer, cover either sides of the polymer substrate membrane. The artificial cornea comprises the polymer substrate membrane, having the enhanced layer and suppressed layer.

In this invention, the plasma induced graft polymerization includes the sequential steps of introducing gaseous plasma to a reactor, exposure to gas plasma treatment to a substrate, the annexation of monomer material to the substrate and degassing the reactor.

In the plasma induced graft polymerization of the invention, the monomer concentration, reaction time and reaction temperature on the polymer material surface can be changed. Different membranes can be prepared with a different quantity of surface material grafted and the membrane property can be modified to form a heterobifunctional membrane.

In this invention, the adopted polymer substrates are the well-known polymer material, such as silicone rubber (SR) or polyurethane (PU). In those methods mentioned above, the exposure gas is Ar or $N_2$ gas. The appendant monomer in the preparing process is selected from one of the following compounds: 2-hydroxyethyl methacrylate (HEMA), acrylic acid (AA), 2-methacryloyloxyethyl phosphorylcholine (2-MPC), methacrylic acid (MA), MPC-co-butyl methacrylate (BMA, BM). The polyethylene oxide (PEO) oligomer is selected from one of 600, 1000, 3350, 4000, or 20000 molecular weights.

In this invention, the heterobifunctional biomedical membrane is prepared by the plasma induced graft polymerization technique. The monomer materials annexation can be described as: a grafted enhanced layer covering the frontal side of a polymer substrate, and a grafted suppressed layer covering the back side of the polymer substrate. The enhanced layer can be selected from one of the following compounds: polyacrylic acid, hydroxyethyl methacrylate (HEMA), MPC-co-butyl methacrylate (BMA, BM) or polymethacrylic acid. However, this modified surface can be re-bonded to the collagen after the grafted polymer materials. The suppressed layer can be selected from one of the polymer materials such as acrylic acid (AA), 2-hydroxyethyl methacrylate (HEMA), 2-methacryloyloxyethyl phosphorylcholine (2-MPC) or methacrylic acid (MA), and then re-bonded to different molecular weights of polyethylene oxide (PEO). The surface structure of heterobifunctional biomedical membrane is shown in FIG. 1 on any one of the (above-mentioned) polymer materials grafted as the enhanced layer, if required, the collagen can be re-bonded over its surface. In preparing the collagen membrane covering the enhanced layer, the frontal side of heterobifunctional biomedical membrane can possess the function of accelerating cell attachment growth. Due to the enhanced layer accelerating cell attachment growth and the suppressed layer inhibiting cell and protein attachment, the biomedical membrane in this invention has a heterobifunctional property.

In the above mentioned method, the reaction conditions of the plasma induced graft polymerization, such as gas pressure, reaction temperature, reaction time, and the added monomer concentration can influence the interactive reaction and graft polymerization. The gas plasma treatment uses the Ar gas or $N_2$ gas, the selected plasma treatment power is 5 watt to 150 watt, and the better power is 40 watt to 80 watt. Plasma treatment time generally is controlled between 5 and 600 seconds, and the better time is 30 seconds to 100 seconds. The plasma operation pressure generally is controlled in the range from 10 mtorr to 1200 mtorr, and the better treating pressure is 100 mtorr to 1000 mtorr. Generally, the selected solution is 1% to 95% composition as the membrane polymerizes and grafts to any one monomer, the better concentration is 10% to 75%. With regard to collagen, the selected solution contains 50–500 μg/ml collagen for collagen bonding on the surface of the membrane, and the better concentration is 150–300 μg/ml. The concentration of the polyethylene oxide is 0.01 M–0.1 M, and the better concentration is 150–300 μg/ml. The concentration of the polyethylene oxide is 0.01 M–0.1 M and the better composition is 0.03–0.08 M. Generally, 2-cyclohexy-3-(2-morphoilnoethyl) carbodiimide (CMC) is added as a coupler when the membrane is bonded with collagen or polyethylene oxide (PEO) of the biomolecule.

In this invention, the heterobifunctional biomedical membrane is prepared to form the artificial cornea implantation having the polymer substrate selected from medical silicone rubber or polyurethane (PU). The process for preparing the membrane includes plasma induced graft polymerization. The prepared heterobifunctional membrane is shown as FIG. 2. But, the heterobifunctional membrane in this invention includes the enhanced layer and suppressed layer. These different two layers are separately prepared by plasma induced graft polymerization. According to this invention, the heterobifunctional biomedical membrane comprises the polymer substrate membrane, the enhanced layer and the suppressed layer. The polymer substrate membranae is covered with a different membrane layer on either side forming the enhanced layer or suppressed layer. The basic structure of heterobifunctional biomedical membrane, constructed with the different membrane layers is defined as:

(1) monomer $_1$ (M) -graft polymerization (g)-polymer substrate-monomer $_2$ (N) graft polymerization (g).

(2) monomer $_1$ (M) -graft polymerization (g) -polymer substrate-monomer $_2$ (N) graft polymerization (g)-PEO(A).

(3) collagen (B)-monomer$_1$ (M)-graft polymerization (g)-polymer substrate-monomer $_2$(N) graft polymerization (g).

(4) collagen (B) -monomer$_1$ (M) -graft polymerization (g)-polymer substrate-monomer $_2$(N) graft polymerization (g)-PEO(A).

In this invention, the polymer substrates are selected from one of the well-known polymer materials, such as silicon rubber (SR) or polyurethane (PU). The appended monomer$_1$ (M) was selected from one of the following compounds: 2-hydroxyethyl methacrylate (HEMA), acrylic acid (AA), methacrylic acid (MA), and the appendant monomer $_2$(N) was selected from one of MPC-co-butyl methacrylate (BMA, BM), 2-methacryloyloxyethyl phosphorylcholine (2-MPC), methacrylic acid (MA), or acrylic acid (AA). The polyethylene oxide (PEO) oligomer is selected from one of 600, 1000, 3350, 4000, or 20000 molecular weights.

The heterobifunctional biomedical membrane is prepared by the plasma induced graft polymerization technique in this invention. The process includes the following sequential steps:

(1) the polymer membrane is laid on the electrode plate of a plasma reactor, (2) controlling the temperature of the electrode plate at 10° C. by a chilling recirculation method, (3) conducting the plasma gas at 5 liters/min. into the reactor for 1–5 minutes after the system is evacuated to 5 mtorr, (4) switching off the inlet gas valve and evacuating the system to 5 mtorr. The plasma is treated in the above mentioned sequence 2–3 times for 5 to 600 seconds per sequence. The plasma treatment power is 5–150 watts and the operating pressure is controlled under 10 mtorr to 1200 mtorr. Then the membrane that is re-exposed in oxygen for 20 minutes is loaded into the disc-type reaction membrane, as shown in FIG. 3. A chosen monomer $_1$(M) solution is loaded into the A reaction tank (1) and a chosen monomer $_2$ (N) is loaded into the B reactor. During the graft polymerization, the degassing operations, chilling, extraction, and molten should be executed many times, and the membrane is laid in a closed bottle. The reaction then proceeds in a isothermal oscillating tank under 75° C. for over 48 hours. After the reaction ends, the prepared membrane is taken out and set into a sample bottle which includes the deionized water, and then the membrane is treated using ultrasonic oscillation for 24 hours to eliminate the homopolymer on the membrane surface and then dried by evacuating. Next, the membrane is set into the reaction membrane (3). A collagen solution that contains the coupler is injected to the A reactor and the reaction proceeds for 24 hours under 0° C. Finally, the membrane is taken out and processed by cleaning and extracted drying, thus forming a heterobifunctional biomedical membrane. Upon the surface of this membrane, the characteristic properties analysis, in vitro study and animal in vivo study are also performed. The obtained results exhibit a very good performance. The concentration of monomer $_1$(M) solution and monomer $_2$ (N) solution is 5 to 95% water solution or ethanol solution.

Moreover, the study demonstrates that the developed product has good transparency, hydrophilicity and high biological compatibility, thus exhibiting the high potential in the application field of artificial cornea.

In order to appraise and work out the heterobifunctional biomedical membrane in this invention, an ATR-FTIR is used for surface functional group analysis of this membrane. An element surface characteristic assay (ESCA) is used for the survey scan and high resolution spectrum. The physical properties variations, such as surface elements analysis and contact angle, can be measured also. The in vitro test includes the explanation of the corneal epithelial cell (CEC) with animal cornea that is obtained from the New Zealand rabbit and the biological compatibility analysis between the cell and material. The penetrating keratoplasty operation is performed on a living experiment animal. The modification membrane is mended on the surface of the rabbit cornea, as shown in FIG. 4.

The in vitro and in vivo tests that incorporate growth migration slit lamp microscopy and immunofluoresence stain to examine CEC attachment and growth analysis, is used to evaluate the created biological response of the animal CEC mended heterobifunctioanl biomedical membrane. Herein, FIG. 5 is a study result of the ESCA and surface element analysis carried out with the heterobifunctional biomedial membrane. This result explains the membrane's physical properties. The grafted membrane exhibits absorption peaks at 3300 $cm^{-1}$ and 1720 $cm^{-1}$ which represents the hydroxylic group and carbonyl group respectively in the membrane. These absorption peaks represent the specific functional groups of the HEMA, AA, MA and MPC. The high bond energy (at 287.7 eV and 290 eV) of the grafted membrane exhibits the absorption peaks. These peaks respectively exhibit the membrane which possesses the hydroxylic group and carbonyl group structures. The membrane exhibits high resolution absorption peaks at 286.4 eV, 287.7 eV and 289.1 eV after its surface is grafted with PEO or collagen. These absorption peaks represent that this membrane contains an amine group, hydroxyl group and amide group respectively, as the ESCA shows in FIG. 6. The ratio of these characterized peak heights can be obtained from the curve fitting of high energy bonding values, as listed in Table 1. Thus, the hydrophilicity is improved after this membrane graft polymerization. These results are shown in Table 2, at various contact angles.

In in vitro study, the silicone rubber grafted HEMA membrane and silicone rubber grafted AA-collagen membrane are used for the CEC growth migration analysis. According to the results shown in FIG. 7, a great deal of suspending cells can be found on the silicone rubber surface when the cornea tissue grows on the migrated membrane. The SR-g-pMPC membrane can inhibit completely the CEC growth and migration. The CEC proliferation and attachment analysis proceeded for 8 hours. The CEC attached to the surfaces of the SR-g-pAA-collagen membrane and SR-g-HEMA membrane. A little amount of CEC still can attach on the surface of the SR-g-pAA-PEO membrane that is prepared by the PEO, of 4000 to 20000 of molecular weight. The analysis result is shown in FIG. 8. The SR-g-pMPC can inhibit completely the CEC attachment.

The morphology of CEC is the same as that of normal CEC as it attaches on the surfaces of SR-g-pHEMA membrane and SR-g-pAA collagen. FIG. 9 exhibits the morphology of CEC attached onto the surface of a membrane. No matter whether the attachment of the CEC was on the surface of the control or on the surface of SR-g-pAA, they all produced the abnormal pseudopodium. The CEC attaching on the surface of SR-g-pAA-PEO membrane of 4000 and 20000 of molecular weight, which exhibits a different status from that of the general CEC. The CEC attaching on the surface of SR-g-AA-HEMA membrane or SR-g-pAA-collagen membrane exhibits the same growth curve as that of the normal CEC. FIG. 10 shows the CEC growth curve, which indicates that the modified surface provides a good environment for CEC attachment and growth.

In in vivo study, the control of SR-g-pAA-collagen membrane was implanted onto the rabbit cornea for three weeks. The depth of the anterior chamber (AC) was measured by slit lamp microscopy. It was found that the depth of the AC disappeared for the control gradually. The depth of rabbit AC becomes as the SR-g-pAA-PEO or SR-g-pHEMA membrane, with 4000 or 20000 of molecular weight, is implanted. The depth of the rabbit AC was still normal when the SR-g-pMPC was used.

The growth of CEC was investigated by immunofluoresence stain after the membrane was implanted onto rabbit cornea for three weeks. It is found that, except the application results of SR-g-pHEMA membrane and SR-g-pAA-collagent membrane which are better, the results others are worse. The analysis results are shown in FIG. 12.

The modified membrane, collagen-pAA-g-SR-g-pMPC, is implanted onto the rabbit cornea for three weeks, it is investigated by slit lamp microscopy and immunofluoresence stain. It is found that the CEC growth and the depth of rabbit AC is in a normal state, as shown in FIG. 13. From the above mentioned information, the heterobifunctional membrane possesses the feasibility of the artificial corneal applications in this invention.

In order to depict this invention process, the following implemented examples are described, but the patent application extent of this invention is not limited.

BRIEF DESCRIPTION OF THE DRAWINGS

The file of this patent contains at least one drawing executed in color. Copies of this patent with color drawings will be provided by the Patent and Trademark Office upon request and payment of the necessary fee.

| 1. . .A-reactor; | 2. . .B-reaction tank; |
| 3. . .membrane; | 4. . .Shaker; |
| 5. . .Water bath; | 6. . .O-ring; |
| 7. . .Clamp; | 8. . .Plug |

Figure 4:
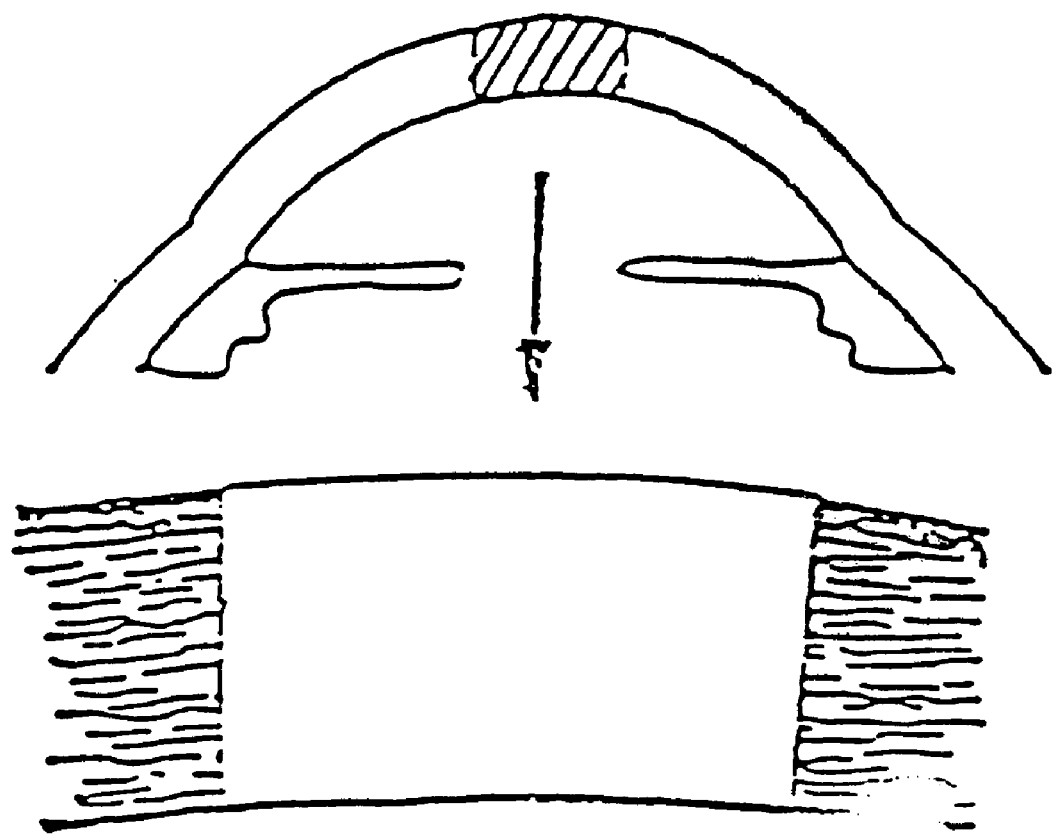
Figure 5:
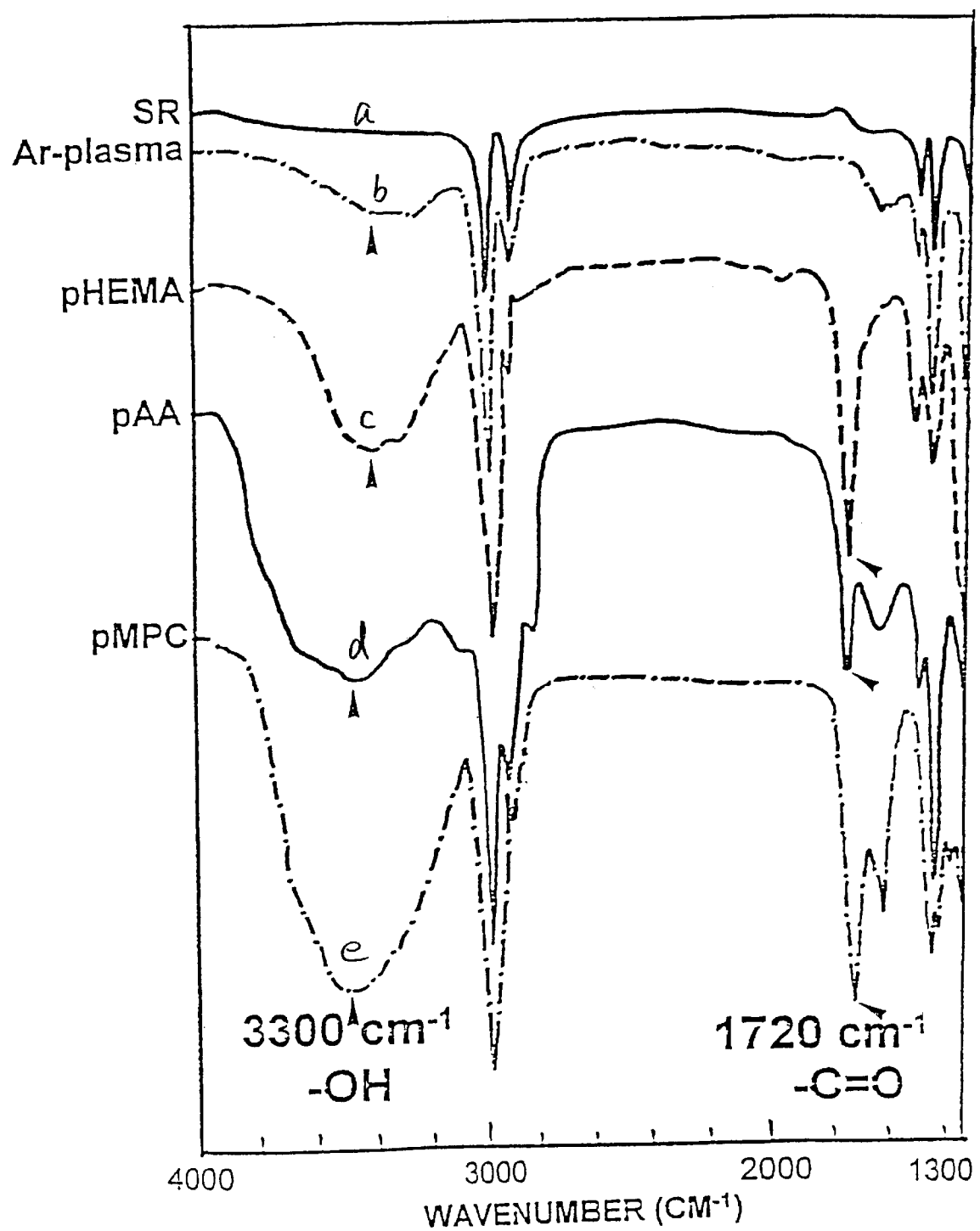
Figure 6:
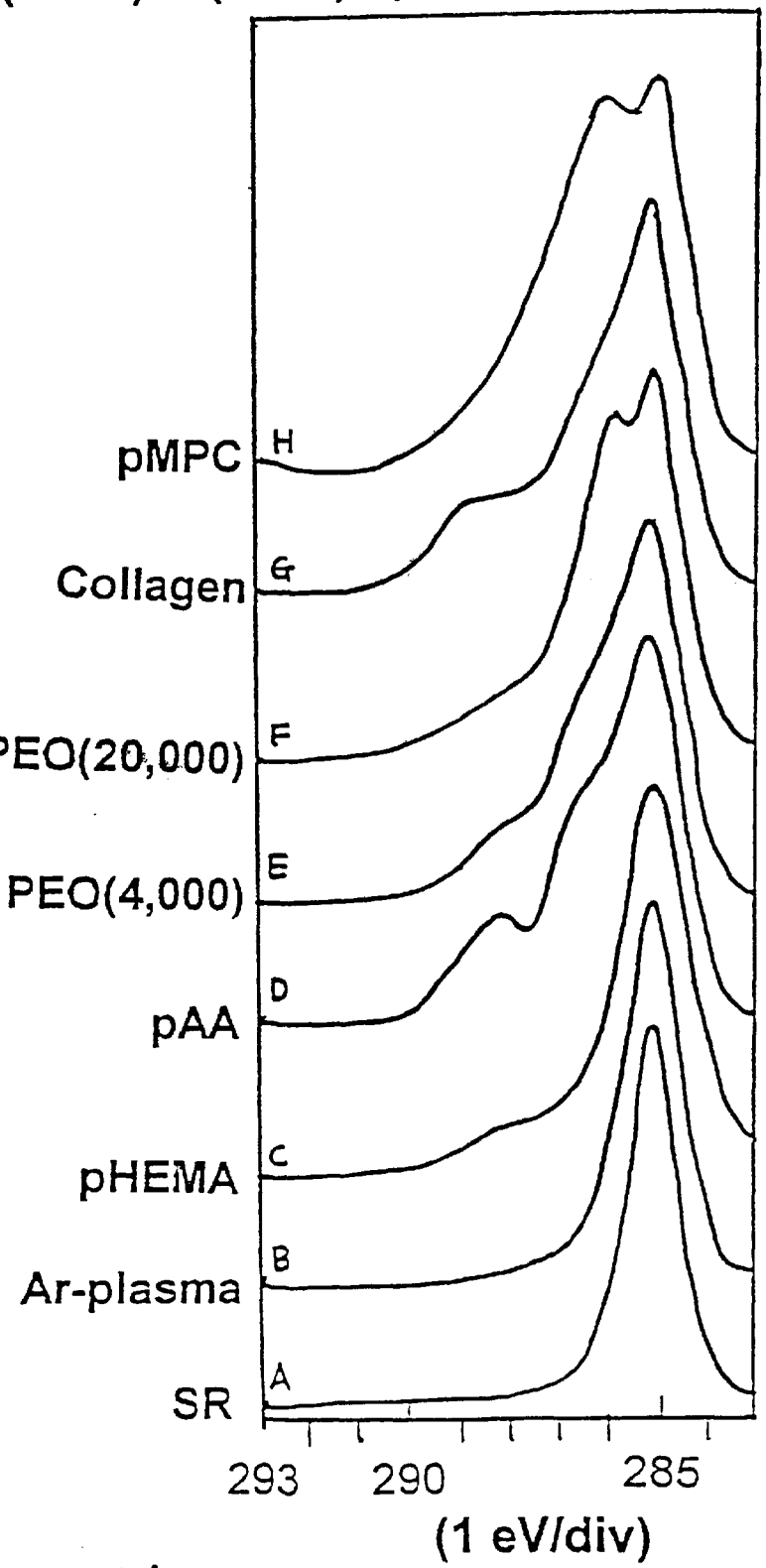

FIG. 4. The full layer cornea implantation operation position on the surface of Rabbit cornea FIG. 5. Spectra of ATR-FTIR for various surfaces of silicone rubber membranes a. control b. Ar-plasma treatment c. SR-g-pHEMA, 75 $\mu g/cm^2$ d. Sr-g-pAA, 420 $\mu g/cm^2$ e. SR-g-pMPC, 175 $\mu g/cm^2$ FIG. 6. High resolution spectra of ESCA for various surfaces of silicone rubber membrane.

a. control b. Ar-plasma treatment c. SR-g-pHEMA, 75 $\mu g/cm^2$ d. SR-g-pAA, 420 $\mu g/cm^2$ e. SR-g-pAA-PEO, Mw=4,000 f. SR-g-pAA-PEO, Mw=20,000 g. SR-g-pAA-collagen, 10 $\mu g/cm^2$ h. SR-g-pMPC, 175 $\mu g/cm^2$

Figure 7A:
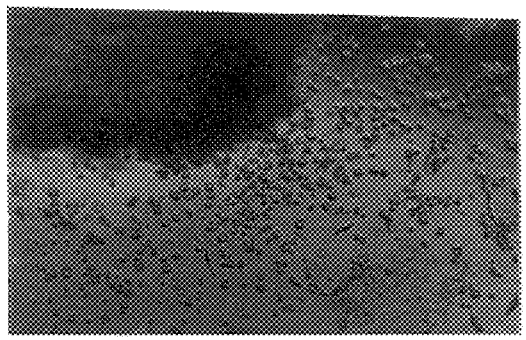

FIG. 7A the analysis of CEC growth and migration in vitro study with control membrane.

Figure 7B:
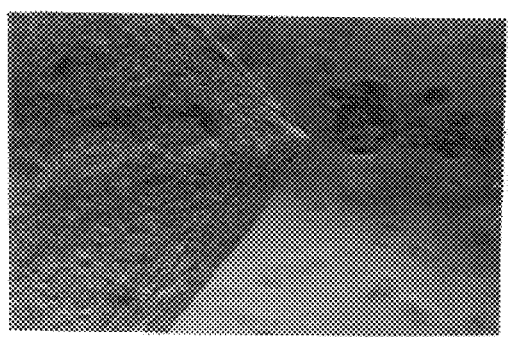

FIG. 7B the analysis of CEC growth and migration in vitro study with Ar-plasma treated membrane.

Figure 7C:
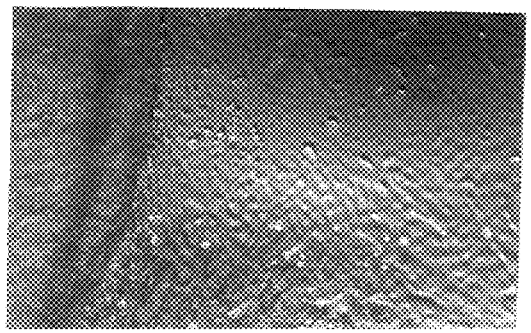

FIG. 7C the analysis of CEC growth and migration in vitro study with SR-g-pHEMA membrane (75ug/cm$^2$)

Figure 7D:
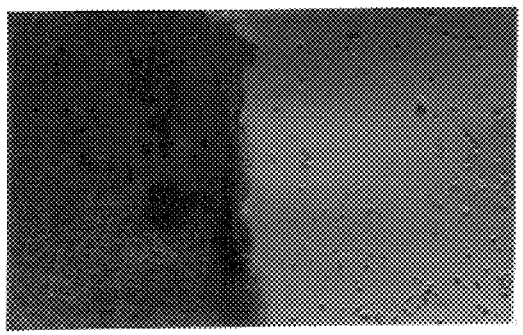

FIG. 7D the analysis of CEC growth and migration in vitro study with SR-g-pMPC membrane (175ug/cm$^2$)

Figure 7E:
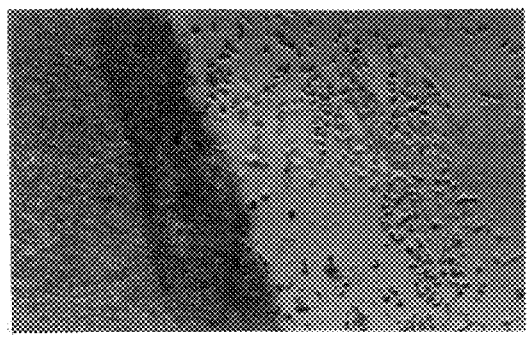

FIG. 7E the analysis of CEC growth and migration in vitro study with SR-g-pAA membrane (420ug/cm$^2$)

Figure 7F:
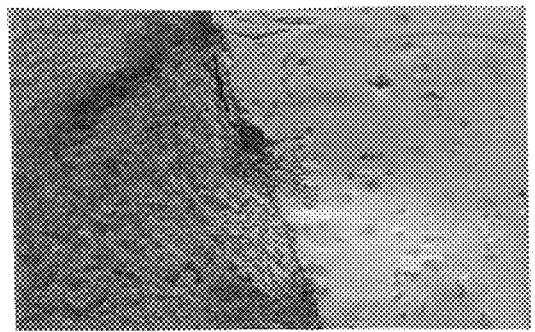

FIG. 7F the analysis of CEC growth and migration in vitro study with SR-g-pAA-PEO membrane (Mw=4,000)

Figure 7G:
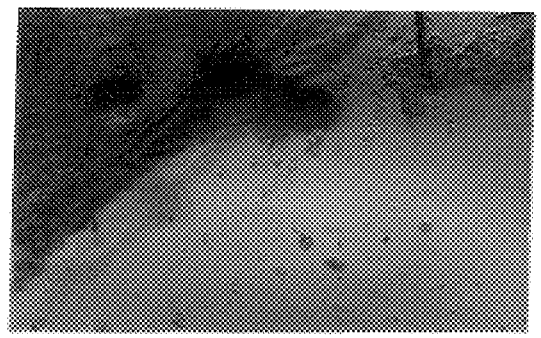

FIG. 7G the analysis of CEC growth and migration in vitro study with SR-g-pAA-PEO membranae (Mw=20,000).

Figure 7H:
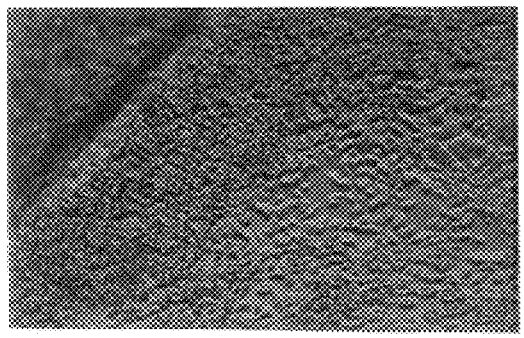

FIG. 7H the analysis of CEC growth and migration in vitro study with SR-g-pAA-collagen membrane (10 ug/cm$^2$)

Figure 8:
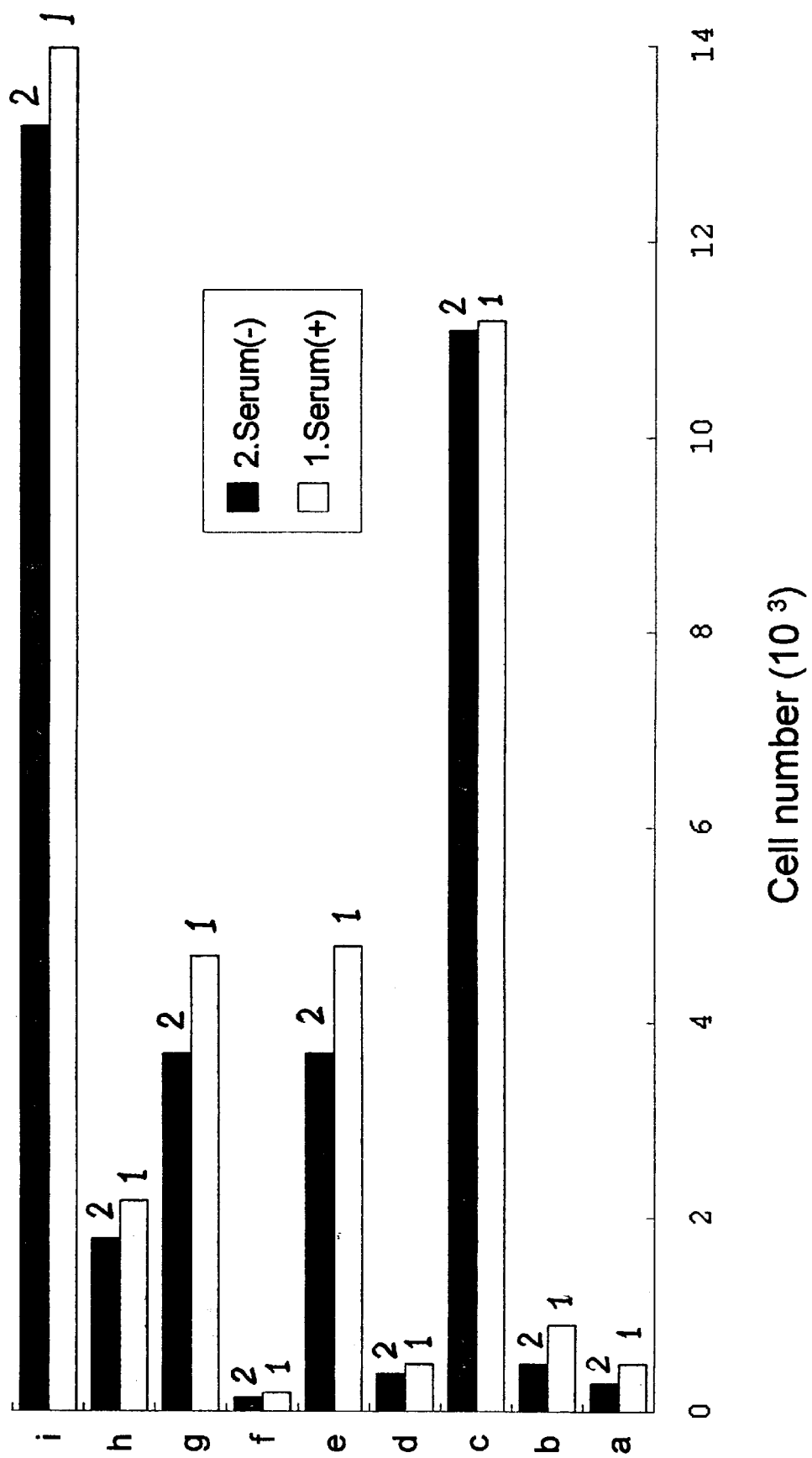

FIG. 8. the CEC attachment analysis in vivo study.

2. with serum 1. without serum a. control b. Ar-plasma treatment c. SR-g-pHEMA, 75 μg/cm$^2$ d. pure, pHEMA e. SR-g-pAA, 420 μg/cm$^2$ f. SR-g-pMPC, 75 μg/cm$^2$ g. SR-g-pAA-PEO, Mw=4,000 h. SR-g-pAA-PEO, Mw=20,000 i. SR-g-pAA-collagen, 10 μg/cm$^2$

Figure 9A:
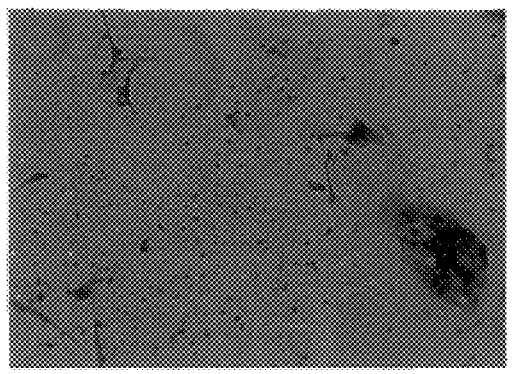

FIG. 9A the morphology of corneal epithelial cell attaching on the surface of control membrane.

Figure 9B:
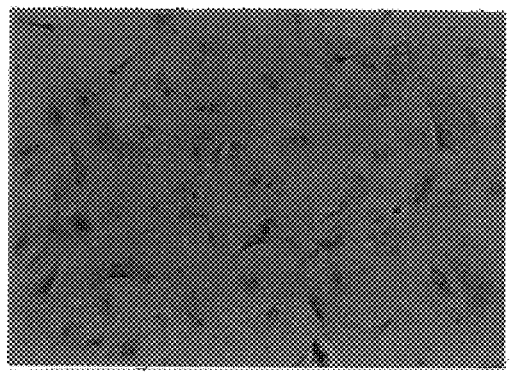

FIG. 9B the morphology of corneal epithelial cell attaching on the surface of Ar-plasma treated membrane.

Figure 9C:
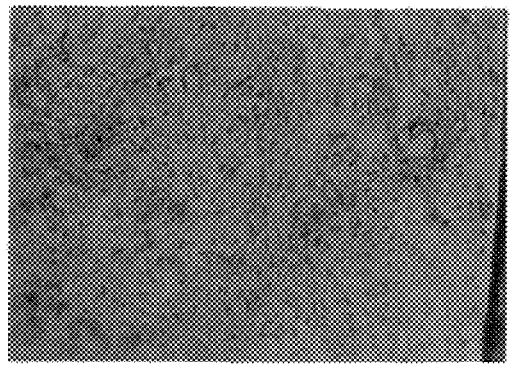

FIG. 9C the morphology of corneal epithelial cell attaching on the surface of SR-g-pHEMA membrane (75ug/cm$^2$).

Figure 9D:
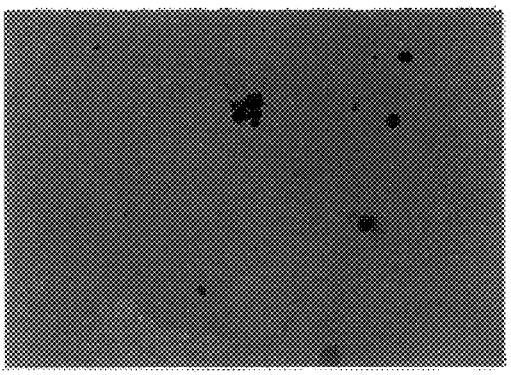

FIG. 9D the morphology of corneal epithelial cell attaching on the surface of SR-g-pMPC membrane (175/ug/cm$^2$).

Figure 9E:
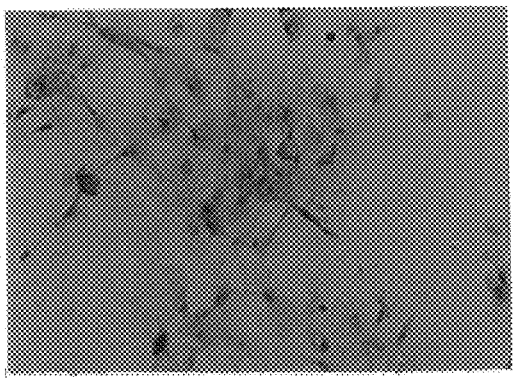

FIG. 9E the morphology of corneal epithelial cell attaching on the surface of SR-g-pAA membrane (420ug/cm$^2$).

Figure 9F:
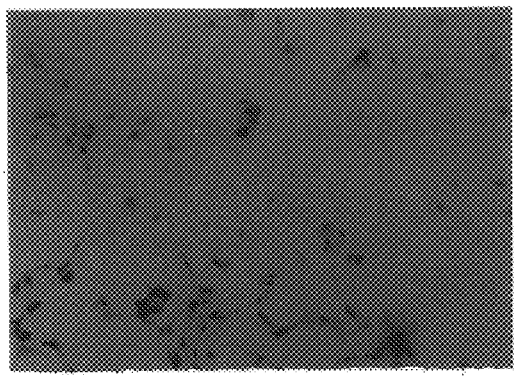

FIG. 9F the morphology of corneal epithelial cell attaching on the surface of SR-g-pAA-PEO membrane (Mw=4,000).

Figure 9G:
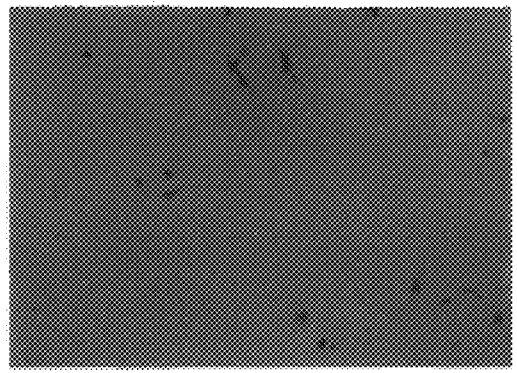

FIG. 9G the morphology of corneal epithelial cell attaching on the surface of SR-g-pAA-PEO membrane (Mw=20,000).

Figure 9H:
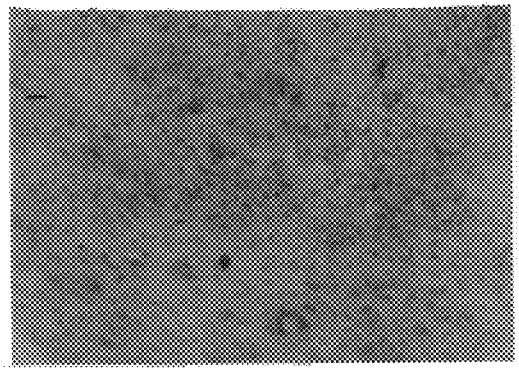

FIG. 9H the morphology of corneal epithelial cell attaching on the surface of SR-g-pAA-collagen membrane (10 ug/cm$^2$).

FIG. 10. The growth analysis of CEC in vitro study (10$^5$ cells/well).

a. control b. Ar-plasma treatment c. SR-g-pHEMA d. SR-g-pAA-collagen e. SR-g-pAA f. pure g. SR-g-pAA-PEO'MW=4000 h. SR-g-pAA-PEO'MW=20,000 i. SR-g-pMPC

FIG. 11A the slit lamp microphotographs in vivo study with control membrane.

FIG. 11B the slit lamp microphotographs in vivo study with SR-g-pHEMA membrane (75ug/cm$^2$).

FIG. 11C the slit lamp microphotographs in vivo study with SR-g-PMPC membranae (175ug/cm$^2$).

FIG. 11D the slit lamp microphotographs in vivo study with SR-g-pAA-PEO membrane (Mw=4,000).

FIG. 11E the slit lamp microphotographs in vivo study with SR-g-pAA-PEO membrane (Mw=20,000).

FIG. 11F the slit lamp microphotographs in vivo study with SR-g-pAA-collagen membrane (loug/cm$^2$).

FIG. 12A the immunofluorescence staining microphotography in vivo study with controlled SR membrane.

FIG. 12B the immunofluorescence staining microphotography in vivo study with SR-g-pHEMA membrane (75ug/cm$^2$).

FIG. 12C the immunofluorescence staining microphotography in vivo study with SR-g-pMPC membrane (175ug/cm$^2$).

FIG. 12D the immunofluorescence staining microphotography in vivo study with SR-g-pAA-PEO membrane (Mw=4,000).

FIG. 12E the immunofluorescence staining microphotography in vivo study with SR-g-pAA-PEO membrane (Mw=20,000).

FIG. 12F the immunofluorescence staining microphotography in vivo study with SR-g-pAA-collagen membrane (loug/cm$^2$).

Figure 13A:
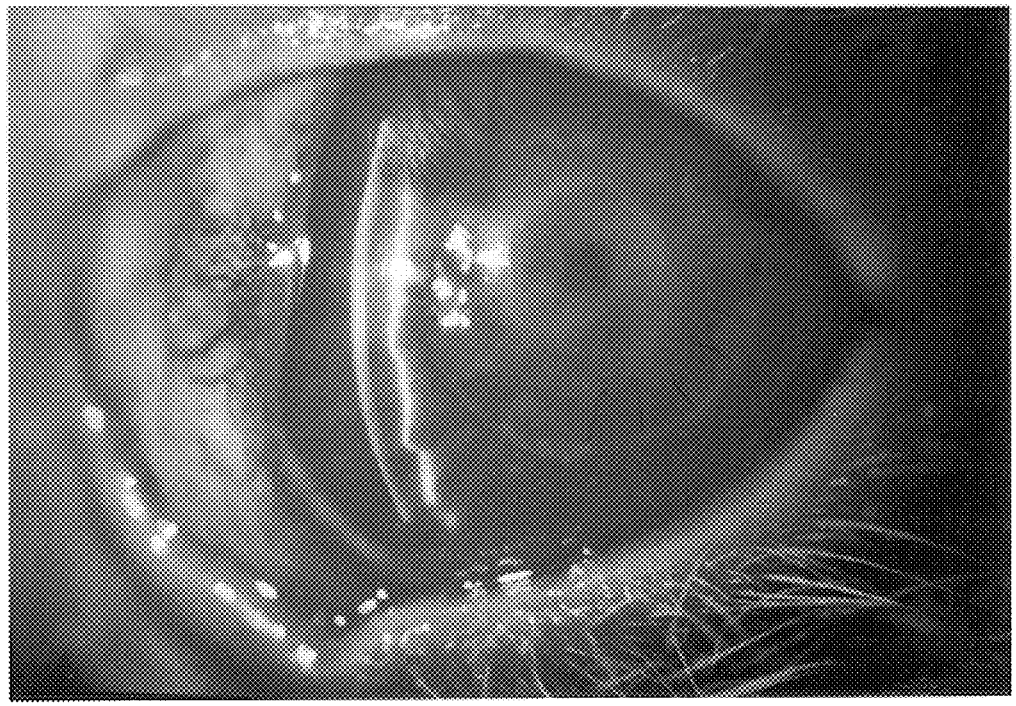

FIG. 13A slit lamp photographs for the implanted membrane that owns the SR-g-pAA-collagen on frontal face and the SR-g-pMPC on rear face onto rabbit corneal.

Figure 13B:
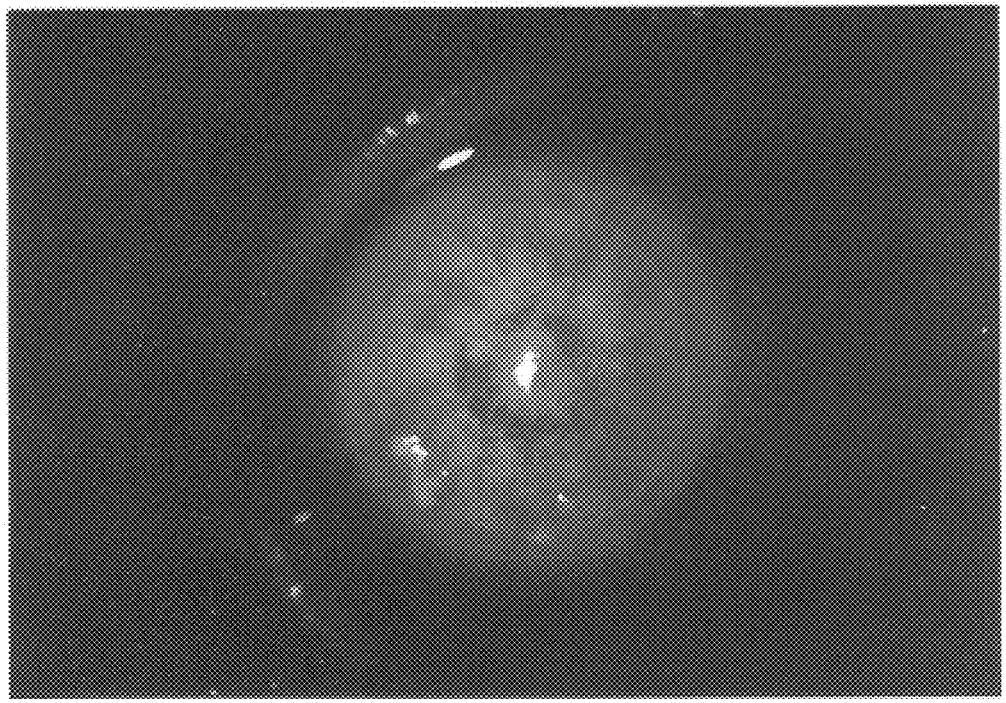

FIG. 13B immunofluorescence staining photographs for heterobi-functional SR of the implanted membrane that owns the SR-g-pAA-collagen on frontal face and the SR-g-pMPC on rear face onto rabbit corneal.

FIG. 14. Schematic diagram of spin coating model for preparation of artificial cornea with silicon rubber.

Table 1. The absorption peak ratio of functional groups on various surfaces of SR by ESCA.

Table 2. The contact angle for various SR surface after the monomer modified surface.

DETAILED DESCRIPTION OF THE INVENTION

THE IMPLEMENTED EXAMPLES

Example 1

The preparation of collagen-pAA-g-SR-g-pMPC

Figure 1:
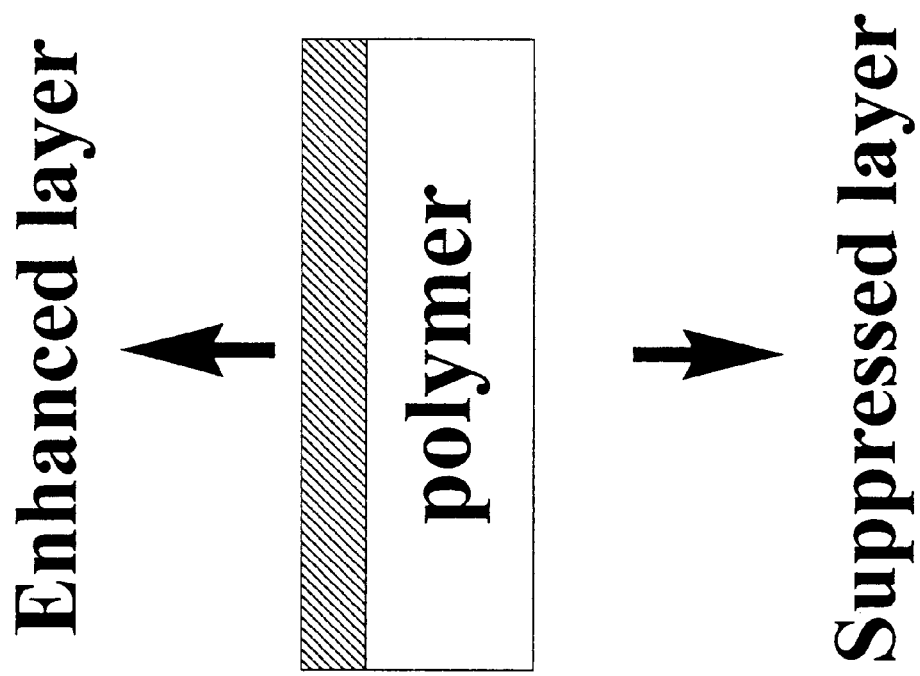
FIG. 1. The surface structure of heterobifunctional membrane
Figure 2:
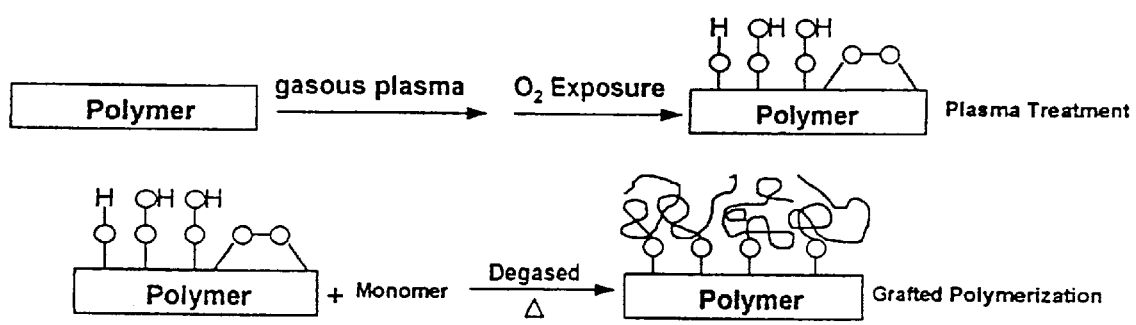
FIG. 2. The schematic diagram of the plasma grafted polymerization.
Figure 3:
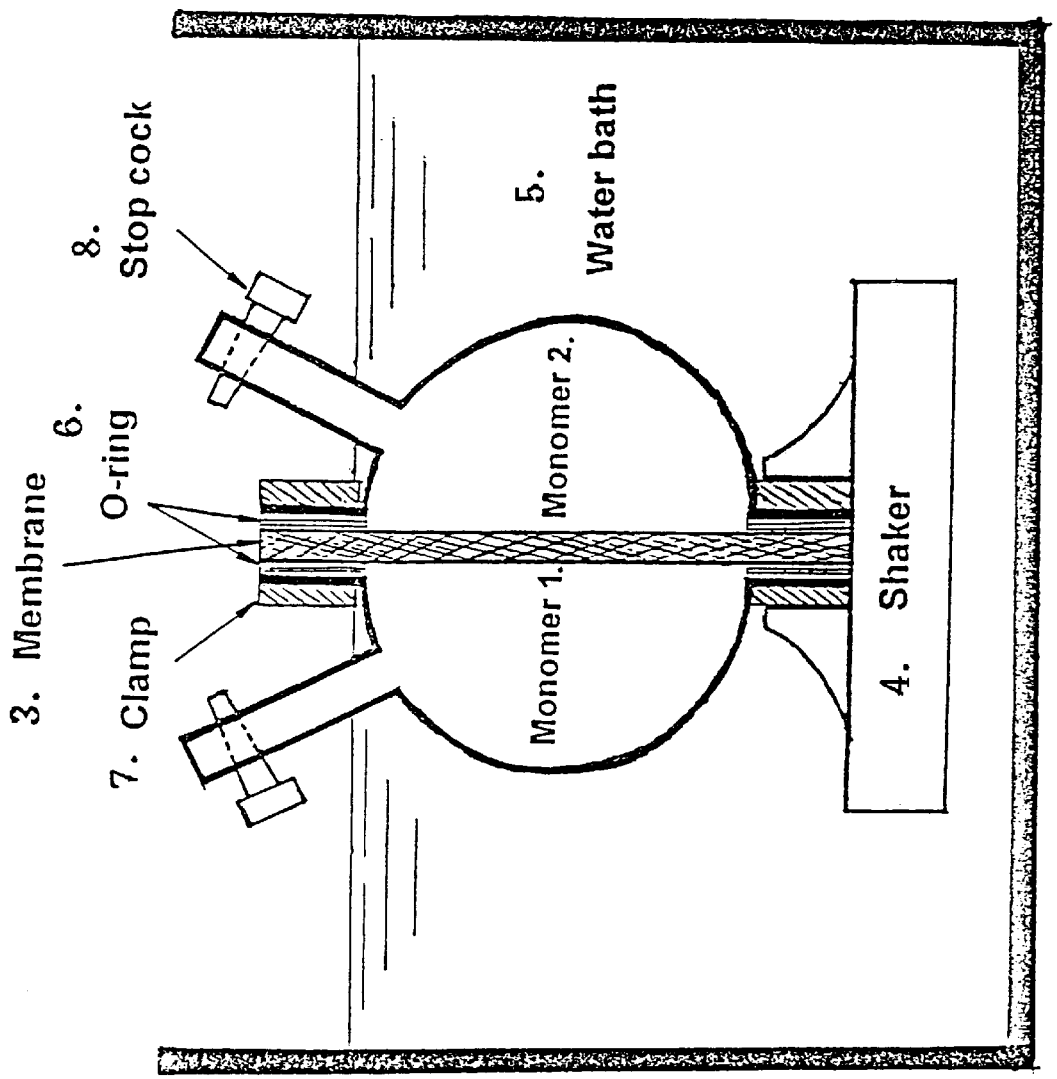
FIG. 3. Disc reactor

Its process can be described as: with sequential procedure, (1). the polymer membrane is loaded into the plasma reactor, (2). controlling the temperature of the electrode plate at 10° C. by the chilling recirculation method, (3). introducing the plasma gas at 5 liters/min. into the reactor for 1–5 minutes after the system is evacuated to 5 mtorr, (4). switching off the inlet gas valve and evacuating the system to 5 mtorr. The plasma is treated by the above mentioned sequence 2–3 times. The polymer membrane then is treated with a 60 watt, 200 mtorr Ar-plasma for 60 seconds in the following step. The membrane is taken out from the reactor and set into the disc reactor after the oxygen gas is introduced into the reactor for 20 min. The schematic diagram is show in FIG. 3. The 15 ml AA monomer solution is set into the A reactor and 15 ml of the 2-MPC monomer is set into the B reactor. The system executes chilling, extraction, and defrost degas operations 6 times and then switches off the bottle mouth under evacuation. The reactor is set into a closed bottle, and the reaction process in an isothermal shaking tank under 75° C. for over 48 hours. After the reaction ends, the prepared membrane is taken out and set into a sample bottle which includes the deionized water, and then the membrane is treated in ultrasonic oscillation for 24 hours to eliminate the homopolymer on the membrane surface and dried by evacuating. Next, the membrane is set into the reaction membrane (3). A collagen solution that contains 0.1M, 200 μ g/ml 2-cyclohexy-3-(2-morphoilnoethyl) carbodiimide (CMC) is injected to the A reactor and the reaction proceeds for 24 hours under 0° C. Finally, the membrane is taken out and processed by cleaning and extracted drying. Thus, a modified surface membrane can be obtained.

Example 2

The preparation of the collagen-pAA-g-SR-g-pAA-PEO membrane

With the same plasma treatment conditions and reaction process as used in example 1, the prepared membrane is taken out from the reactor. Two 15 ml AA monomer solutions are loaded into the reaction tank A and B respectively. The system executes chilling, extraction, and defrost degas operations 6 times and then switches off the bottle mouth under evacuation. The reactor is set into a closed bottle. The reaction proceeds in a isothermal shaking tank under 75° C. for over 48 hours. The different membranes that contain different surface grafted amounts can be obtained when the monomer concentration, reaction period and reaction temperature are varied. After the reaction ends, the prepared membrane is taken out and set into a sample bottle which includes the deionized water, and then the membrane treated in ultrasonic oscillation for 24 hours to eliminate the homopolymer on the membrane surface and drying by evacuating. Next, the membrane is set into the Disc type reactor. The 200 μg/ml collagen solution is injected into the A reactor, and the 0.05M polyethylene glycol solutions which possess 600, 1000, 3350, 4000, 20000 molecular weights are injected into the B reactor separately. In both tanks, the 0.1 M CMC solutions used as the coupler are added to both reaction tanks. The reaction proceeds for 24 hours under 0° C. Finally, the membrane is taken out and processed by the cleaning and extracted drying. Thus, a modified surface membrane can be obtained.

Example 3

The preparation of the collagen-pMA-g-SR-g-pMPC membrane

With the same plasma treatment conditions and reaction process as that used in Example 1, 15 ml MA monomer solution is loaded into the A tank and 15 ml MPC monomer solution is loaded in the B tank. The system executes chilling, extraction, and defrost degas operations 6 times and then switches off the bottle mouth under evacuation. The reactor is set into a closed bottle, and the reaction proceeds in an isothermal shaking tank under 75° C. for over 48 hours. The prepared membrane is taken out and set into a sample bottle which includes the deionized water, and then the membrane is treated in ultrasonic oscillation for 24 hours to eliminate the homopolymer on the membrane surface and dried by evacuating. Next, the membrane is loaded into the reactor again. A collagen solution that contains 0.1M, 200 μ g/ml 2-cyclohexy-3-(2-morphoilnoethyl) carboniimide (CMC) is injected to the A reactor. The reaction proceeds for 24 hours under 0° C. Finally, the membrane is taken out and processed by cleaning, and extracted drying. Thus, a modified surface membranae can be obtained.

Example 4

The preparation of the collagen-pMA-g-SR-g-pMA-PEO membrane

With the same plasma treatment conditions and reaction process as that used in Example 1, two 15 ml AA monomer solutions are loaded into the reaction tank A and B respectively. The system executes chilling, extraction, and defrost degas operations 6 times and then switches off the bottle mouth under the evacuated condition, the reactor is set into a closed bottle, and the reaction proceeds in an isothermal shaking tank under 75° C. for over 48 hours. The prepared membrane is taken out and set into a sample bottle which includes the deionized water, and then the membrane is treated by ultrasonic oscillation for 24 hours to eliminate the homopolymer on the membrane surface and dried by evacuating. Next, the membrane is loaded into the reactor again, a solution that contains 200 μ g/ml collagen is injected into the A tank, the 0.1M CMC monomer and 0.05M polyethylene glycol solution which possess 600, 1000, 3350, 4000, 20000 molecular weights is injected into the B reactor separately. The reaction proceeds for 24 hours under 0° C. Finally, the membrane is taken out and processed by cleaning and extracted drying. Thus, the modified surface membrane can be obtained.

Example 5

The preparation of the pHEMA-g-SR-g-pMPC membrane

According to the same plasma treatment conditions and reaction process as that used in Example 1, the 15 ml HEMA monomer solution is loaded into the A tank and 15 ml MPC monomer solution is loaded into the B tank for preparing the modified surface membrane.

Example 6

The preparation of the HEMA-g-SR-g-pAA-PEO membrane

According to the same plasma treatment conditions and reaction process as used in Example 1, 15 ml HEMA monomer is loaded into the A tank and 15 ml AA monomer solution is loaded into the B tank. The membrane is loaded into the reactor again for proceeding with the grafted polymerization after it is dried by evacuating. The 0.1M CMC monomer and 0.05M polyethylene glycol solution which possess 600, 1000, 3350, 4000, 20000 molecular weights is injected into the B reactor separately. The reaction proceeds for 24 hours under 0° C., finally, the membrane is taken out and processed by cleaning and extracted drying. Thus, a modified surface membrane can be obtained.

Example 7

The preparation of the pHEMA-g-SR-g-pMA-g-PEO membrane

According to the same plasma treatment conditions and reaction process as used in Example 1, 15 ml HEMA monomer solution is loaded into the A tank and 15 ml MA monomer solution is loaded into the B tank. The membrane is loaded into the reactor for proceeding with the grafted polymerization after it is dried by evacuating. A 0.1M CMC monomer and 0.05M polyethylene glycol solution which possess 600, 1000, 3350, 4000, 20000 molecular weights is injected into the B reactor separately. The reaction proceeds for 24 hours under 0° C. Finally, the membrane is taken out and processed by cleaning and extracted drying. Thus, a modified surface membrane can be obtained.

Examples 8–16

The preparation of the PU membrane

With the same plasma treatment conditions and reaction process as that depicted in Example 1, the monomer used is PU and a modified surface PU membrane can be obtained.

Example 17

The preparation of the curvetuve type silicone rubber

According to the size of the artificial cornea, the plasma induced graft polymerization membrane is loaded into a Spin coating model that is shown in FIG. 14. This model is heated for preparing the artificial cornea under the selected conditions: radian is 0.599 mm, radius is 7.159 mm and spin velocity is 100 rpm.

TABLE 1

The ratio of functional groups on various surfaces of silicone rubbber by ESCA

| Sample | C—H (285) | C—N (286.4) | C—O (287.7) | —HN—C=O (289.1) | O—C=O (290) |
|---|---|---|---|---|---|
| Control | 100.0 | — | — | — | — |
| Ar-plasma* | 77.81 | — | 15.21 | — | 6.98 |
| pHEMA(75 μg) | 53.01 | — | 33.37 | — | 13.63 |
| pAA(420 μg) | 35.02 | — | 42.27 | — | 22.71 |
| PEO(Mw 4,000) | 31.47 | 10.2 | 43.28 | — | 15.05 |
| PEO(Mw 20,000) | 15.96 | 6.4 | 65.47 | — | 12.17 |
| Collagen(10 μg) | 43.37 | — | 16.73 | 27.15 | 12.75 |
| pMPC(175 μg) | 40.61 | 21.10 | 10.14 | — | 28.15 |

μg/cm² is unit, *60 W, 200 mtorr, 60 sec

TABLE 2

The contact angle for various Sr surface

| Sample | Contact angle (degree) |
|---|---|
| Controlled SR | 105 ± 8 |
| Ar-plasma* | 95 ± 5 |
| pAA(175 μg) | 48 ± 3 |
| pHEMA(75 μg) | 52 ± 4 |
| pMPC(175 μg) | 54 ± 4 |
| Collagen(10 μg) | 54 ± 4 |
| PEO(Mw4,00) | 63 ± 3 |
| PEO(Mw20,00) | 58 ± 5 |

*60 W, 60 s, 200 mtorr

What is claimed it:

1. A heterobifunctional biomedical membrane comprising a polymer substrate layer;
   a suppressed layer on a first surface of said polymer substrate layer; and
   an enhanced layer on a second surface of said polymer substrate layer;
   said enhanced layer is selected from the group consisting of polyacrylic acid having a layer of collagen thereon, polymethacrylic acid having a layer of collagen thereon, hydroxyethyl methacrylate, hydroxyethyl methacrylate having a layer of collagen thereon, and 2-methacryloyloxyethyl phosphorylcholine-co-butyl methacrylate having a layer of collagen thereon;
   said suppressed layer is selected from the group consisting of polyacrylic acid, polyacrylic acid having a polyethylene oxide layer thereon, polymethacrylic acid having a polyethylene oxide layer thereon, hydroxyethyl methacrylate having a polyethylene oxide layer thereon, 2-methacryloyloxyethyl phosphorylcholine, 2-methacryloyloxyethyl phosphorylcholine having a polyethylene oxide layer thereon, 2-methacryloyloxyethyl phosphorylcholine-co-butyl methacrylate, and 2-methacryloyloxyethyl phosphorylcholine-co-butyl methacrylate having a polyethylene oxide layer thereon.

2. The heterobifunctional biomedical membrane as defined in claim 1, wherein the polyethylene oxide layer is formed from a polyethylene oxide oligomer having a molecular weight of 600, 1000, 3350, 4000, or 20,000.

3. The heterobifunctional biomedical membrane as defined in claim 1, wherein the polymer substrate is silicone rubber or polyurethane.

4. A process for preparing the heterobifunctional biomedical membrane as defined in claim 1, comprising exposing said polymer substrate to a plasma gas to form a treated polymer substrate;
   graft polymerizing a first monomer selected from the group consisting of acrylic acid, methacrylic acid, hydroxyethyl methacrylate, and 2-methacryloyloxyethyl phosphorylcholine-co-butyl methacrylate onto said first surface of said treated polymer substrate,
   forming a collagen layer on said polymerized acrylic acid, said polymerized methacrylic acid and said 2-methacryloyloxyethyl phosphorylcholine-co-butyl methacrylate and optionally forming a collagen layer on said polymerized hydroxyethyl methacrylate to form said enhanced layer,
   graft polymerizing a second monomer selected from the group consisting of acrylic acid, methacrylic acid, hydroxyethyl methacrylate, 2-methacryloyloxyethyl phosphorylcholine, and 2-methacryloyloxyethyl phosphorylcholine-co-butyl methacrylate on said second surface of said treated polymer substrate, and
   forming a polyethylene oxide layer on said polymerized methacrylic acid, and said polymerized hydroxyethyl methacrylate and optionally forming a polyethylene oxide layer on said polymerized acrylic acid, said 2-methacryloyloxyethyl phosphorylcholine and said 2-methacryloyloxyethyl phosphorylcholine-co-butyl methacrylate to form said suppressed layer.

5. The process for preparing the heterobifunctional biomedical membrane as defined in claim 4, wherein said plasma gas is selected from the group consisting of argon gas, nitrogen gas and oxygen gas.

6. The process for preparing a heterobifunctional biomedical membrane as defined in claim 4,
   wherein said polymer substrate is exposed to said argon gas, nitrogen gas, and oxygen gas plasma at a treatment power of 5 to 150 watts, for 5 to 600 seconds, and at a plasma operation pressure of 10 to 1200 mtorr.

7. The process for preparing a heterobifunctional biomedical membrane as defined in claim 4, wherein said first monomer and said second monomer layers are formed on said substrate using a monomer solution which is 1 to 95% water solution or ethanol solution.

8. The process of preparing a heterobifunctional biomedical membrane comprising exposing a polymer substrate to a plasma gas to form a treated polymer substrate;
   graft polymerizing a first monomer selected from the group consisting of acrylic acid, methacrylic acid, hydroxyethyl methacrylate, and 2-methacryloyloxyethyl phosphorylcholine-co-butyl methacrylate onto a first surface of said treated polymer substrate,
   graft polymerizing a second monomer selected from the group consisting of acrylic acid, methacrylic acid, hydroxyethyl methacrylate, 2-methacryloyloxyethyl phosphorylcholine, and 2-methacryloyloxyethyl phosphorylcholine-co-butyl methacrylate on a second surface of said treated polymer substrate, and
   forming a collagen layer on said polymerized first monomer layer to form said enhanced layer,
   wherein said heterobifunctional biomedical membrane comprises
   said polymer substrate layer;
   a suppressed layer on said first surface of said polymer substrate layer; and an enhanced layer on said second surface of said polymer substrate layer;

said enhanced layer is selected from the group consisting of polvacrylic acid having a layer of collagen thereon, polymethacrylic acid having a layer of collagen thereon, hydroxyethyl methacrylate having a layer of collagen thereon, and 2-methacryloyloxyethyl phosphorylcholine-co-butyl methacrylate having a layer of collagen thereon;

said suppressed layer is selected from the group consisting of polvacrylic acid, polyacrylic acid having a polyethylene oxide layer thereon, polymethacrylic acid having a polyethylene oxide layer thereon, hydroxyethyl methacrylate having a polyethylene oxide layer thereon, 2-methacryloyloxyethyl phosphorylcholine, 2-methacryloyloxyethyl phosphorylcholine having a polyethylene oxide layer thereon, 2-methacryloyloxethyl phosphorylcholine-co-butyl methacrylate, and 2-methacryloyloxyethyl phosphorylcholine-co-butyl methacrylate having a polyethylene oxide layer thereon.

9. The process for preparing the heterobifunctional biomedical membrane as defined in claim 8, further comprising forming a polyethylene oxide layer on the polymerized monomer layer on the second surface of said treated polymer substrate to form said suppressed layer.

10. The process for preparing a heterobifunctional biomedical membrane as defined in claim 8, wherein said step of forming the collagen layer further comprises introducing said polymer substrate having said first monomer layer thereon to a collagen solution comprising from 150–300 μg/ml collagen to form said collagen layer.

11. A process for preparing a heterobifunctional biomedical membrane comprising laying a polymer substrate on an electrode plate in a plasma reactor, chilling said electrode plate, evacuating said plasma reactor, conducting plasma gas into said plasma reactor, evacuating said plasma reactor, exposing said treated polymer substrate to oxygen, placing said treated polymer substrate that has been exposed to oxygen into a reaction tank, said reaction tank containing a first reactor and a second reactor separated by a reaction membrane, introducing a first monomer solution into said first reactor of said reaction tank, graft polymerizing said first monomer onto a first side of said treated polymer substrate, introducing a second monomer solution into said second reactor of said reaction tank, graft polymerizing said second monomer onto a second surface of said treated polymer substrate to form a heterobifunctional biomedical membranes wherein said heterobifunctional biomedical membrane comprises said polymer substrate layer;

a suppressed layer on said first surface of said polymer substrate layer; and an enhanced layer on said second surface of said polymer substrate layer;

said enhanced layer is selected from the group consisting of polvacrylic acid having a layer of collagen thereon, polvmethacrylic acid having a layer of collagen thereon, hydroxyethyl methacrylate, hydroxyethyl methacrylate having a layer of collagen thereon, and 2-methacryloyloxyethyl phosphorylcholine-co-butyl methacrylate having a layer of collagen thereon;

said suppressed layer is selected from the group consisting of polyacrylic acid, polyacrylic acid having a polyethylene oxide layer thereon, polvmethacrylic acid having a polyethylene oxide layer thereon, hydroxyethyl methacrylate having a polyethylene oxide layer thereon, 2-methacryloyloxyethyl phosphorylcholine, 2-methacryloyloxyethyl phosphorylcholine having a polyethylene oxide layer thereon, 2-methacryloyloxyethyl phosphorylcholine-co-butyl methacrylate, and 2-methacryloyloxyethyl phosphorylcholine-co-butyl methacrylate having a polyethylene oxide layer thereon.

12. The process of preparing the heterobifunctional biomedical membrane as defined in claim 11, further comprising the steps of cleaning and drying said membrane, returning said membrane to the reaction tank, injecting a collagen solution into said first reactor of said reaction tank, forming a layer of collagen on said polymerized first monomer to form an enhanced layer, injecting polyethylene oxide solution into said second reactor of said reaction tank, and forming a layer of polyethylene oxide on said polymerized second monomer layer to form a suppressed layer.

13. The process of preparing the heterobifunctional biomedical membrane as defined in claim 12, wherein said plasma gas is conducted through said plasma reactor at 5 to 150 watts, 10 to 1200 mtorr, and for 5 to 600 seconds, wherein said each of said first monomer solution and said second monomer solution has a concentration of from 1 to 95%, and wherein said collagen solution contains from 150–300 μg/ml collagen.

* * * * *